United States Patent [19]

Hill et al.

[11] Patent Number: 4,764,509

[45] Date of Patent: Aug. 16, 1988

[54] PHARMACEUTICAL COMPOSITIONS CONTAINING DI-GOLD PHOSPHINE

[75] Inventors: David T. Hill, North Wales; Randall K. Johnson, Ardmore, both of Pa.

[73] Assignee: SmithKline Beckman Corporation, Philadelphia, Pa.

[21] Appl. No.: 86,208

[22] Filed: Aug. 17, 1987

Related U.S. Application Data

[63] Continuation of Ser. No. 832,105, Feb. 21, 1986, abandoned, which is a continuation of Ser. No. 736,018, May 20, 1985, abandoned.

[51] Int. Cl.[4] ............................................. A61K 31/66
[52] U.S. Cl. ..................................................... 514/102
[58] Field of Search ......................................... 514/102

[56] References Cited

U.S. PATENT DOCUMENTS 4,057,630  11/1977  Hill ....................................... 514/102

FOREIGN PATENT DOCUMENTS

420151046A3  8/1985  European Pat. Off. .
0164970A2  12/1985  European Pat. Off. .

OTHER PUBLICATIONS

Shaw et al., *Inorganica Chimica Acta*, 123, 213–216 (1986).
Eggleston et al., *Inorganica Chemica Acta*, 108, 221–226 (1985).
Mirabelli et al., *Biochemical Pharmacology*, 35(9), 1435–1443 (1986).
Mirabelli et al., *Biochemical Pharmacology*, 35(9), 1427–1433 (1986).
Mirabelli et al., *J. Med. Chem.*, 29(2), 218–223 (1986).
Hill et al., American Chemical Society Abstract #204 (1986).
Berners-Price et al. American Chemical Society Abstract #244 (1986).
Mirabelli et al., Abstract #1114, Proceedings of AACR, 27, Mar. 1986.
Johnson et al., Abstract #1115, Proceedings of AACR, 27, Mar. 1986.
Hill et al., Abstract #14, American Chemical Society, Sep. 8–13, 1985.
Berners-Price et al., *J. Chem. Soc., Dalton Trans*, 969–974 (1984).
Schmidbaur et al., *Chem. Ber*, 110, 2751–2557 (1977).
Stringer et al., abstract from the 15th Middle Atlantic Regional Meeting of the American Chemical Society, Jan. 7–9, 1981, Washington, D.C.
Struck et al., *J. Med. Chem.*, 9, 414–417 (1966).
Mirabelli et al., *Proceedings of AACR* Mar. 1984, No. 1455, p. 367 (1984).
Mirabelli et al., *Cancer Research, 45, 32–39 (1985)*.
Johnson et al., *Proceedings of AACR* Mar. 1985, No. 1001, p. 254 (1985).
Snyder et al., *Proceedings of AACR* Mar. 1985, No. 1007, p. 255 (1985).
Mirabelli et al., *Proceedings of AACR* Mar. 1985, No. 1008, p. 256 (1985).
Weinstock et al., *J. Med. Chem.*, 17,(1), 139–140 (1974).

*Primary Examiner*—Jerome D. Goldberg
*Attorney, Agent, or Firm*—Carol G. Canter; Edward T. Lentz; Alan D. Lourie

[57] ABSTRACT

Pharmaceutical compositions containing an effective, tumor cell growth-inhibiting amount of such a compound, and a method for treating tumor cells sensitive to such a di-gold phosphine compound which comprises administering a tumor cell growth-inhibiting amount of such a compound to an animal afflicted by said tumor cells.

17 Claims, No Drawings

PHARMACEUTICAL COMPOSITIONS CONTAINING DI-GOLD PHOSPHINE

CROSS REFERENCE TO RELATED APPLICATION

This is a continuation of application Ser. No. 832,105, filed Feb. 21, 1986, now abandoned, which is a continuation of applicaton Ser. No. 736,018, filed May 20, 1985, which is abandoned.

BACKGROUND OF THE INVENTION

This invention relates to novel pharmaceutical compositions containing an effective, tumor cell growth-inhibiting amount of a di-gold phosphine compound, and a method for treating tumor cells sensitive to a di-gold phosphine compound by administering tumor cell growth-inhibiting amounts of such a di-gold phosphine compound to a host animal afflicted by such tumor cells.

Sadler et al., *J. Chem. Soc., Dalton Trans*, 969-974 (1984), propose the synthesis of dichlorobis[1,2-bis(diphenylphosphino)ethane]digold(I), but were unable to isolate the compound. Schmidbaur et al., *Chem. Ber*, 110, 2751-2557 (1977), disclose dichlorobis[1,2 -bis(diphenylphosphino)methane]digold(I). Stringer et al., abstract from the 15th Middle Atlantic Regional Meeting of the American Chemical Society, Jan. 7-9, 1981, Washington, D.C., disclose the synthesis of dichlorobis[1,2-bis (diphenylphosphino)ethane]digold(I), dichlorobis[1,2-bis(diethylphosphino)ethane]digold(I), and diperchlorobis [1,2-bis(diethylphosphino)ethane]-digold(I), and state that these three compounds were evaluated for activity in adjuvant-induced arthritis in the Charles River Wistar rat. However, there is no disclosure in the Stringer, et al. reference that such compounds actually have antiarthritic or any other therapeutically useful biological activity. Struck et al., *J. Med. Chem.*, 9, 414-417 (1966), disclose cytotoxic activity for 1,2-bis(diphenylphosphino)ethane which is used as a starting material for preparing some of the compounds of the pharmaceutical compositions and methods of treatment of the subject invention. None of the aforementioned references disclose or suggest the pharmaceutical compositions and/or methods of treatment of the subject invention.

SUMMARY OF THE INVENTION

This invention relates to a pharmaceutical composition which comprises an effective, tumor cell growth-inhibiting amount of an active ingredient and an inert, pharmaceutically acceptable carrier or diluent, wherein said composition is useful for inhibiting the growth of animal tumor cells sensitive to the active ingredient, and wherein the active ingredient is a compound of the formula:

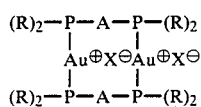  Formula (I)

wherein
R is the same and is phenyl or ethyl;
A is the same and is straight or branched alkanediyl chain of one to six carbon atoms; and
X is the same and is halo.

Another aspect of this invention relates to a method of inhibiting the growth of animal tumor cells sensitive to a compound of Formula (I) which comprises administering to an animal afflicted with said tumor cells, an effective, tumor cell growth-inhibiting amount of a compound of Formula (I).

DETAILED DESCRIPTION OF THE INVENTION

All the compounds of Formula (I) can be prepared by methods available to one skilled in the art.

Generally, the, compounds of Formula (I), wherein it is chloro, can be prepared by reacting one mole of the appropriate ligand of the formula:

  Formula (II)

with one mole of the appropriate gold complex of the formula:

  Formula (III)

wherein R and A are as defined above, in a nonreactive organic solvent.

All the necessary Formula (II) ligands are available from commercial sources, for example, from Strem Chemicals, Inc., Newburyport, Mass.

The Formula (III) gold complexes, wherein X is chloro, are conveniently prepared by reacting the appropriate ligand of Formula (II) with chloroauric acid tetrahydrate which has been reduced by treatment with thiodiglycol. Formula (III) gold complexes, wherein X is chloro, may also be conveniently prepared by reacting the appropriate ligand of Formula (II) directly with chloroauric acid hydrate in an appropriate non-reactive organic solvent.

Formula (III) complexes, wherein X is bromo, are prepared by reacting the appropriate ligand of Formula (II) with bromoauric acid hydrate (which is commercially available, for example from Strem Chemicals, Inc., Newburyport, Mass.) which has been reduced by treatment with thioidiglycol, or by reacting the appropriate ligand of Formula (II) directly with bromoauric acid hydrate in an appropriate non-reactive organic solvent. Alternatively, Formula (III) complexes, wherein X is bromo, are prepared by reacting the appropriate compound of Formula (III), wherein X is chloro, with sodium bromide in an appropriate organic solvent, such as aqueous ethanol or DMF.

Formula (I) compounds, wherein X is bromo, are prepared by reacting one mole of the appropriate compound of Formula (III), wh.erein X is bromo, with one mole of the appropriate compound of Formula (II). Alternatively, Formula (I) compounds, wherein X is bromo, are prepared by reacting the appropriate Formula (I) compound, wherein X is chloro, with sodium bromide in an appropriate organic solvent, such as aqueous ethanol or DMF.

Formula (I) compounds, wherein X is iodo, are prepared by reacting the appropriate Formula (I) compound, wherein X is chloro or bromo, with sodium iodide in an appropriate organic solvent, such as acetone.

As stated above, the compounds of Formula (I) have tumor cell growth-inhibiting activity which has been demonstrated in at least one animal tumor model.

P388 lymphocytic leukemia is currently the most widely used animal tumor model for screening for antitumor agents and for detailed evaluation of active compounds. This tumor system is widely accepted as an antitumor agent screening tool because it is sensitive to virtually all of the clinically active antineoplastic agents; quantitative and reproducible; amenable for large-scale screening; and predictive for activity in other animal tumor models. Drugs that are highly active in intraperitoneal (ip) P388 leukemia are generally active in other tumor models as well. The antitumor activity of the compounds of Formula (I) is demonstrated in the P388 leukemia mouse model employing the following protocol:

$10^6$ P388 leukemia cells are inoculated ip in $B6D2F_1$ mice. Twenty-four hours later, if the tumor inoculum proves to be free of bacterial contamination (as determined by 24 hours incubation in thioglycollate broth), animals are randomized into groups of 6 and housed in shoebox cages. The compound to be evaluated is dissolved in a minimal volume of either N,N-dimethylacetamide (DMA) or 95% ethanol (depending upon solubility). An equal volume of saline is added; if the drug comes out of solution an equal volume of polyethoxylated castor oil is added and then saline qs to a concentration such that the desired dose is delivered in 0.5 ml. The final concentration of DMA, ethanol and polyethoxylated castor oil is 10 percent. Dilutions for lower doses are made with saline so there is a decreasing proportion of organic solvents in the vehicle with decreasing dosage These vehicles provide soluble formulations (or suspensions). Formulations are prepared immediately prior to injection. The compound is administered ip on Days 1 through 5 (i.e. treatment is initiated 24 hrs after tumor inoculation). Each experiment includes three groups of 6 animals as untreated controls and animals treated with a positive control, cisplatin, at two dose levels. Animals are weighed as a group on Days 1, 5 and 9 and average weight change (Δ wt.) is used as a reflection of toxicity. Each experiment also includes an inoculum titration—groups of 8 mice inoculated ip with $10^5$ to $10^0$ P388 leukemia cells. The titration is used to calculate cell kill achieved by treatment with drugs. Animals are monitored daily for mortality and experiments are terminated after 45 days. The endpoint is median survival time (MST) and, increase in lifespan (ILS) which is the percentage of increase in MST relative to untreated controls. Untreated controls inoculated ip with $10^6$ P388 leukemia cells generally survive for a median of 10 or 11 days. A drug is considered active if it produces $\geq 25$ percent ILS.

A summary of the evaluation of two compounds of Formula (I) in the in vivo ip P388 model is shown in the following Table A.

TABLE A $$\begin{array}{c} (R)_2-P-A-P-(R)_2 \\ |\quad\quad\quad | \\ Au^\oplus X^\ominus Au^\oplus X^\ominus \\ |\quad\quad\quad | \\ (R)_2-P-A-P-(R)_2 \end{array}$$ Formula (I)

| Compound Number | R | A | X | MTD[a] (mg/kg) | ILS (max)[b] (%) |
|---|---|---|---|---|---|
| 1 | phenyl | $(CH_2)_2$ | Cl | 8 | 81/91/55 |
| 2 | ethyl | $(CH_2)_2$ | Cl | 16 | 29 |

[a] maximally tolerated dose for B62DF female mice on an ip qDX5 regimen.
[b] maximum increase in lifespan produced in mice bearing ip P388 leukemia (figures separated by slashes indicate data generated in separate experiments).

Based on the data set forth in Table A, compounds of Formula (I) showed significant antitumor activity in the in vivo ip P388 leukemia tumor assay.

The cytotoxic activity of a Formula (I) compound was evaluated in vivo using B16 melanoma cells. In this system, groups of eight $B6D2F_1$ mice are inoculated ip with 0.5 ml of a 10% (w:v) brei of B16 melanoma prepared from pooled sc tumors excised at 14–21 days from $C67B_1/6$ donor mice. Daily treatment is begun 24 hours after tumor implantation and is continued daily for ten (10) days. The route of drug administration is ip. The mice are monitored daily for survival for sixty (60) days. Antitumor activity is assessed by prolongation of median survival time. An ILS of $\geq 25\%$ indicates activity in this tumor model.

A summary of the results of the in vivo ip B16 melanoma assay is shown in Table B.

TABLE B

| Compound No.[a] | MTD (mg/kg)[b] | ILS (%)[c] |
|---|---|---|
| 1 | 4 | 35 |

[a] see Table A for structure.
[b] maximally tolerated dose for $B6D2F_1$ mice on a ip qD × 10 regimen.
[c] maximum increase in lifespan produced in mice bearing ip B16 melanoma.

The pharmaceutical compositions of this invention comprise an effective tumor cell growth-inhibiting amount of a compound of Formula (I) and an inert pharmaceutically acceptable carrier or diluent. These compositions are prepared in dosage unit form appropriate for parenteral administration.

Compositions according to the invention for parenteral administration include sterile aqueous or non-aqueous solutions, suspensions or emulsions. The composition may be in the form of a solution of the active ingredient in a minimal volume of dimethylacetamide or ethanol, for example 5% v/v, brought up to volume with peanut oil or normal saline solution. Polyethoxylated castor oil, for example 2 to 5% v/v, may also be used to solubilize the active ingredient. In addition, the composition may be in the form of a slurry with, for example, hydroxypropyl cellulose or other suitable suspending agent. As an emulsifying agent, lecithin for example may be used. The composition may also be provided in the form of a sterile solid which can be dissolved in a sterile injectable medium immediately before use.

Freireich et al., *Cancer Chemo. Rept.*, 50, 219–244 (1966), compared the quantitative toxicity of 18 anticancer drugs in six species after correcting the data to a uniform schedule of treatment for five consecutive days. This analysis demonstrated that mouse, rat, dog, human, monkey and man have essentially the same maximum tolerated dose (MTD) when compared on a basis of mg/m² of body surface area. The study suggested that Phase I clinical trials could be safely initiated at a dose one-third the animal MTD. The mouse was as useful as any other species in this regard on which to base the calculation. The appropriate therapeutically effective dose for any compound of the invention can therefore be determined readily by those skilled in the art from simple experimentation with laboratory animals, perferably mice.

It will be appreciated that the actual preferred dosages of the compounds of Formula (I) used in the compositions of this invention will vary according to the particular compound being used, the particular composition formulated, the mode of administration and the particular site, host and disease being treated. The route of internal administration should be selected to ensure that an effective tumor cell growth-inhibiting amount of the compound of Formula (I) contacts the tumor. Optimal dosages for a given set of conditions can be ascertained by those skilled in the art using conventional dosage determination tests in view of the above experimental data. For parenteral administration the dose generally employed is from about 5 to about 20 mg/m$^2$ of body surface per day for one to five days, repeated about every fourth week for four courses of treatment.

The method for inhibiting the growth of animal tumor cells sensitive to a compound of Formula (I) in accordance with this invention comprises administering to a host animal afflicted with said tumor cells, an effective tumor cell growth-inhibiting amount of a compound of Formula (I). As described above, during the course of treatment the active ingredient will be administered parenterally in an amount selected from about 300 mg to about 1000 mg.

EXAMPLES

The following examples illustrate the chemical preparation of several compounds of Formula (I) which are used in the compositions and methods of this invention and as such are not to be construed as limiting the scope thereof. All temperatures are in degrees Centigrade.

EXAMPLE 1

Dichlorobis[1,2-bis(diphenylphosphino)ethane]digold (a)

μ-[1,2-bis(diphenylphosphino)ethane]bis[chlorogold(I)]

Chloroauric acid hydrate (1.6 g, 3.8 mmol) in ethanol (20 ml) was added to bis(1,2-diphenylphosphino)ethane (1.83 g, 4.5 mmol), obtained from Strem Chemicals, Inc., Newburyport, Mass., in 1:1 chloroform/ethanol (40 ml) maintained at room temperature. After one hour, the white precipitate was collected, dissolved in methylene chloride, filtered and ethanol added to induce precipitation. After standing, the product was collected and dried to give 0.97 g (50%) of the named gold complex which had a melting point (m.p.) of 291°–293°.

(b)
Dichlorobis[1,2-bis(diphenylphosphino)ethane]digold

A solution of 1,2-bis(diphenylphosphino)ethane (2.31 g, 5.8 mmoles), obtained from Strem Chemicals, Inc., Newburyport, Mass., in chloroform (100 ml) was added to a slurry of μ-[1,2-bis(diphenylphosphino)ethane]bis chlorogold) (5.0 g, 5.8 mmoles), prepared as described above, in chloroform (500 ml) maintained at ambient temperature. After 45 minutes, the reaction mixture became homogeneous (clear), and solvent was removed in vacuo. The residue was dissolved in a minimum amount of chloroform and ether was added. After cooling, the precipitate was collected and dried to give 3.0 g (41%) of the named product, m.p. 298°–302°.

EXAMPLE 2

Dichlorobis[1,2-bis(diethylphosphino)ethane]digold (a)

μ-[1,2-Bis(diethylphosphino)ethane]bis[chlorogold(I)]

Chloroauric acid tetrahydrate (7.88 g) in water (35 ml) was reduced by thiodiglycol (5.5 g) in ethanol (12 ml) at 0° in standard fashion. A solution of 1,2-bis (diethylphosphino)ethane (2.06 g), obtained from Strem Chemicals, Inc., Newburyport, Mass., in ethanol (15 ml) was added. After stirrrng for 1 hour, the reaction mixture was poured into 400 ml of ice water and extracted with methylene chloride. The combined extracts were dried (MgSO$_4$), filtered and cooled overnight. The resulting solid was collected and air dried to give 3.0 g of the named product, m.p. 168°–170° C.

(b) Dichlorobis[1,2-bis(diethylphosphino)ethane]digold

Addition of 1,2-bis(diethylphosphino)ethane (0.31 g, 1.49 mmole), obtained from Strem Chemicals, Inc., Newburyport, Mass., in a single portion to a solution of μ-[1,2-bis(diethylphosphino)ethane]bis[chlorogold) (1.0 g, 1.49 mmoles), prepared as described above, in chloroform (200 ml) was carried out and the resultant clear solution was stirred for 30 minutes. The solvent was removed in vacuo, and the residue recrystallized from chloroform/ether to give 1.0 g (77%) of the named product, m.p. 211°–214°.

EXAMPLE 3

By utilizing the procedure of Example 1(b) or Example 2(b) to react the appropriate gold complex of Formula (III) (prepared according to the procedure of Example 1(a) or Example 2(a) by utilizing the appropriate haloauric acid hydrate) with the appropriate ligand of Formula (II), the following compounds of Formula (I) wherein X is chloro or bromo are prepared; and/or by reacting the appropriate Formula (I) compound, wherein X is chloro, with sodium bromide in an appropriate organic solvent, such as aqueous ethanol or DMF, the following Formula (I) compounds wherein X is bromo are prepared; and by reacting the appropriate Formula (I) compound wherein X is chloro or bromo with sodium iodide in an appropriate organic solvent, such as acetone, the following compounds of Formula (I) wherein X is iodo are prepared:

(a) dichlorobis[1,2-bis(diphenylphosphino)methane]digold
(b) dichlorobis[1,2-bis(diphenylphosphino)propane]digold
(c) dichlorobis[1,2-bis(diphenylphosphino)butane]digold
(d) dichlorobis[1,2-bis(diphenylphosphino)pentane]digold
(e) dichlorobis[1,2-bis(diphenylphosphino)hexane]digold
(f) dichlorobis[1,2-bis(diethylphosphino)methane]digold
(g) dichlorobis[1,2-bis(diethylphosphino)propane]digold
(h) dichlorobis[1,2-bis(diethylphosphino)butane]digold
(i) dichlorobis[1,2-bis(diethylphosphino)pentane]digold
(j) dichlorobis[1,2-bis(diethylphosphino)hexane]digold (k) diiodobis[1,2-bis(diphenylphosphino)ethane]digold
(l) dibromobis[1,2-bis(diphenylphosphino)ethane]digold.

EXAMPLE 4

As a specific embodiment of a composition of this invention, an active ingredient, such as one part of the compound of Example 1, is dissolved in 5 parts of dimethylacetamide and 5 parts of polyethoxylated castor oil and then normal saline solution qs, and is administered parenterally in one dose of 5 mg/m² to a host animal afflicted with tumor cells sensitive to that compound.

What is claimed is:

1. A parenteral pharmaceutical composition which comprises an effective tumor cell-growth inhibiting amount of an active ingredient and an inert, pharmaceutically acceptable carrier or diluent, wherein said composition is useful for inhibiting the growth of animal tumor cells sensitive to the active ingredient, and wherein the active ingredient is a compound of the formula:

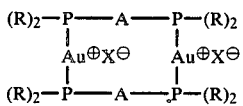

wherein
R is the same and is phenyl or ethyl;
A is the same and is a straight or branched alkanediyl chain of from one to six carbon atoms; and
X is the same and is halo.

2. The composition of claim 1 wherein A is ethane-1,2-diyl.
3. The composition of claim 2 wherein R is phenyl.
4. The composition of claim 2 wherein R is ethyl.
5. The composition of claim 3 wherein X is chloro.
6. The composition of claim 4 wherein X is chloro.
7. The composition of claim 1 which is in a dosage unit form adapted to administer from about 5 to about 20 mg/m² of body surface area.

8. A method of inhibiting the growth of animal tumor cells sensitive to a compound of the formula:

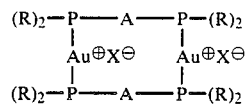

wherein
R is the same and is phenyl or ethyl;
A is the same and is a straight or branched alkanediyl chain of from one to six carbon atoms; and
X is the same and is halo; which comprises parenterally administering to an animal afflicted with said tumor cells, an effective, tumor cell growth-inhibiting amount of said compound.

9. The method according to claim 8 wherein A is ethane-1,2-diyl.
10. The method according to claim 9 wherein R is phenyl.
11. The method according to claim 9 wherein R is ethyl.
12. The method according to claim 10 wherein X is chloro.
13. The method according to claim 11 wherein X is chloro.
14. The method according to claim 8 wherein the amount is selected from a unit dose range of from about 5 to about 20 mg/m² of body surface administered per dose for one to five days.
15. The method according to claim 14 wherein the adminstration is repeated about every fourth week for four courses of treatment.
16. The method according to claim 15 wherein during the course of treatment the amount administered is from about 300 to about 1000 mg.
17. A method of treating tumor cells sensitive to dichlorobis[1,2-bis(diphenylphosphino)ethane]digold in a host animal afflicted with such tumor cells which comprises parenterally administering to the host animal a solution or suspension containing an effective tumor cell growth-inhibiting amount of dichlorobis[1,2-bis(diphenylphosphino)ethane]digold.

* * * * *